(12) United States Patent
Aicher et al.

(10) Patent No.: US 6,554,866 B1
(45) Date of Patent: *Apr. 29, 2003

(54) MONO-CONDYLAR KNEE JOINT PROSTHESIS

(75) Inventors: Martin Aicher, Mahlstetten (DE); Vincent Leclercq, Winterthur (CH); Bernhard G Gyssler, Horgen (CH)

(73) Assignee: Sulzer Orthopedics Ltd., Baar (CH)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/672,583

(22) Filed: Sep. 28, 2000

(30) Foreign Application Priority Data

Oct. 29, 1999 (EP) .............................. 99810980

(51) Int. Cl.⁷ .................................. A61F 2/38
(52) U.S. Cl. ............... 623/20.29; 623/20.3; 623/20.28
(58) Field of Search ................ 623/20.21, 20.28, 623/20.29, 20.3

(56) References Cited

U.S. PATENT DOCUMENTS

| 4,085,466 | A |   | 4/1978 | Goodfellow |        |
|-----------|---|---|--------|------------|--------|
| 4,353,136 | A |   | 10/1982 | Polyzoides |        |
| 5,336,266 | A | * | 8/1994 | Caspari et al. | 623/20 |
| 5,755,801 | A | * | 5/1998 | Walker et al.  | 623/20 |

FOREIGN PATENT DOCUMENTS

| DE | 2660623 C2 | 8/1984 |
| GB | 2312377 A | 10/1997 |
| WO | WO 95/27450 | 10/1995 |

* cited by examiner

*Primary Examiner*—Corrine McDermott
*Assistant Examiner*—Thomas Barrett
(74) *Attorney, Agent, or Firm*—Townsend and Townsend and Crew LLP

(57) ABSTRACT

A mono-condylar knee joint prosthesis that includes a femur part having a convex running surface. The knee joint prosthesis further includes a tibia part having a sliding surface which faces the femur part and an intermediate part which is introduced between the femur part and the tibia part during implantation. The intermediate part has two bearing surfaces, namely a first, concave bearing surface for cooperating with the convex running surface of the femur part as well as a second bearing surface for cooperating with the sliding surface of the tibia part. A boundary surface is provided at the tibia part which bounds the sliding surface of the tibia part and projects pointing in the direction towards the femur part in order to be able to cooperate with a side surface of the intermediate part. The boundary surface which is provided at the tibia part is formed to be curved in the shape of an arch, and the intermediate part has a side surface which is curved corresponding to the boundary surface which is provided at the tibia part and which is curved in the shape of an arch.

3 Claims, 3 Drawing Sheets

MONO-CONDYLAR KNEE JOINT PROSTHESIS

BACKGROUND OF THE INVENTION

1. Field of the Invention

The invention relates to a mono-condylar knee joint prosthesis.

2. Description of the Prior Art

Mono-condylar knee joint prostheses are used where it is not the entire joint connection of the knee joint, that is, the medial as well as the lateral joint connection, that is no longer intact, but rather only one half (either the medial or the lateral half), but where however the ligaments (collateral ligaments and cruciate ligaments) are still fully intact. In these cases a bi-condylar prosthesis need not be implanted. In this way the bone substance which is present can be spared as far as possible and the ligaments as well can be maintained as far as possible.

A mono-condylar knee joint prosthesis of this kind typically comprises a femur part which has a convex running surface and which is fixed either cement-lessly or cementedly at the femur, which has previously been prepared at one side. Furthermore, a knee joint prosthesis of this kind comprises a tibia part which is fixed correspondingly at the tibia, which has previously been prepared at one side. Between the femur part, which is fixed at the femur and which is typically made of metal, and the tibia part, which is fixed at the tibia and which is likewise typically made of metal, an intermediate part is typically arranged which is typically manufactured of plastic (e.g. of ultra high molecular polyethylene) and is either arranged to be slidingly displaceable on a sliding surface of the tibia part or is arranged to be non-displaceable, that is, fixed, relative to the tibia part.

In a known mono-condylar knee joint prosthesis, such as e.g. is described in U.S. Pat. No. 4,085,466, the intermediate part is substantially freely displaceably arranged on the sliding surface of the tibia part. In a knee joint prosthesis of this kind the entire guiding of the movement must be taken over by the muscle and ligament apparatus. The limiting of the movability of the intermediate part then takes place only through the muscles and the ligaments, or, respectively, through the soft parts. Since no lateral limiting of the movability of the intermediate part is present, forces in the medial/lateral direction which were previously partly taken up by the menisci or by the bone bearing respectively must likewise be taken up by the muscles and ligaments or by the still intact bone bearing respectively.

In another exemplary embodiment of U.S. Pat. No. 4,085,466 a boundary surface can be provided which laterally bounds the sliding surface. Thus e.g. in a tibia part of the lateral half of the joint connection in the region of the medial boundary of the tibia part (that is, in the region of the eminentia intercondylaris) a boundary surface can be provided at the tibia part which laterally bounds the sliding surface of the tibia part. This boundary surface extends rectilinearly in the anterior/posterior direction and serves as an abutment surface for that side surface of the intermediate part which faces the boundary surface of the tibia part, or, respectively, it serves as a guiding surface along which the intermediate part is guided. This abutment surface can thus take up forces both in the medial (or, respectively, in a replacement of the medial half, in the lateral) direction and also guide the intermediate part in the anterior/posterior direction.

The kinematics of the natural knee joint should not be influenced or modified wherever possible through a mono-condylar knee joint prosthesis. During the implantation of a mono-condylar knee joint prosthesis the articular cartilage and the meniscus are replaced (by the tibia part and the femur part and by the intermediate part respectively); the connection between the meniscus and the bone, which is present in the natural knee joint, is however not present after the implantation since in the mono-condylar knee joint prosthesis the intermediate part is movable without a connection to the tibia part. A guiding is therefore required for the intermediate part in order to be able to follow the physiological displacing of the condyles.

In accordance with more recent recognitions on the kinematics of the human knee joint it is however the case that the femoro-tibial contact point describes a path which cannot be particularly well approximated by a rectilinear path—such as is described above. This means that if the actual path of the femoro-tibial contact point is approximated by a rectilinear path, as is done in the above-described guiding along the boundary surface which extends rectilinearly in the anterior/posterior direction, then the ligament apparatus is stressed more strongly than is the case in the natural, intact knee.

SUMMARY OF THE INVENTION

Here the invention wishes to provide a remedy. It is therefore an object of the invention to propose a mono-condylar knee joint prosthesis which does not have the above-described disadvantages. The prosthesis should on the one hand bring about a guided movement which corresponds as well as possible to the natural movement of the knee, and the muscles and ligaments should be stressed as naturally as possible. On the other hand the prosthesis should also be able to take up forces in the medial/lateral direction so that such forces can be taken up by the prosthesis and then ultimately by the bone, that is, by the tibia, and need not additionally be taken up by the muscles and ligaments or by the intact half of the bone bearing respectively.

The mono-condylar knee joint prosthesis in accordance with the invention thus comprises a femur part having a convex running surface. It further comprises a tibia part with a sliding surface which faces the femur part and an intermediate part which is introduced between the femur part and the tibia part during the implantation. The intermediate part has two bearing surfaces, namely a first, concave bearing surface for cooperating with the convex running surface of the femur part as well as a second bearing surface for cooperating with the sliding surface of the tibia part. A boundary surface is provided at the tibia part which laterally bounds the sliding surface of the tibia part and projects pointing in the direction towards the femur part in order to be able to cooperate with a side surface of the intermediate part. The boundary surface which is provided at the tibia part is formed to be curved in the shape of a spherical segment and the intermediate part has a side surface which is curved correspondingly to the boundary surface which is provided at the tibia part and which is curved in the shape of an arch.

In a preferred exemplary embodiment the boundary surface which is provided at the tibia part is formed to be curved in the shape of a circular segment, and the side surface of the intermediate part is accordingly formed to be curved in the shape of a circular segment.

The boundary surface, which is arcuate, in particular curved in the shape of a circular segment, and the side surface of the intermediate part, which is curved corresponding to this boundary surface, represent a very good approximation to the natural path of the femoro-tibial contact point, through which the muscles and ligaments are stressed similarly as in the natural, intact knee. In addition, forces acting in the lateral/medial direction can be taken up by the prosthesis or ultimately by the tibia respectively and need not be taken up by the muscle and ligament apparatus as in a prosthesis with a freely movable intermediate part.

In a further advantageous exemplary embodiment of the mono-condylar knee joint prosthesis in accordance with the invention the boundary surface which is provided at the tibia part is formed to be convex and the corresponding side surface of the intermediate part is formed to be concave. This is advantageous because the lateral condyle travels through the significantly longer path in a flexion/extension movement than the medial condyle, and the path of the femoro-tibial contact point of the lateral condyle extends particularly well through a movement along a path which is convex, in particular has the convex shape of a circular segment.

In a further advantageous exemplary embodiment the radius of curvature of the boundary surface of the tibia part and accordingly the radius of curvature of the side surface of the intermediate part lies in the range from 30–50 mm. This range comprises the essential range of the radii with which a movement of the femoro-tibial contact point such as is present in the natural knee is approximated.

In a further advantageous exemplary embodiment the width of the tibia part lies in the range from 15–55 mm and the length of the tibia part lies in the range from 35–60 mm. These ranges for the dimensions of the width and length of the tibia part cover the dimensions of the tibia most frequently occurring in humans.

Finally, in a further advantageous exemplary embodiment the arcuate side surface of the intermediate part extends over an angle of arc which lies in the range from 25°–45°. It is thereby ensured that the meniscus part has a sufficient size in order to ensure a sufficiently large contact surface between the running surface of the femur part and the bearing surface of the intermediate part.

DETAILED DESCRIPTION OF SPECIFIC EXEMPLARY EMBODIMENTS

Figure 1:
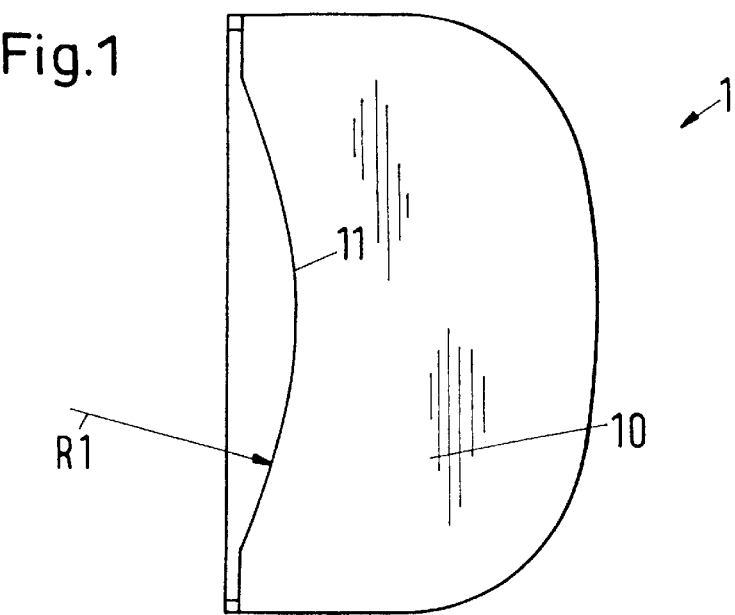
FIG. 1 is a plan view of an exemplary embodiment of a tibia part of a mono-condylar knee joint prosthesis in accordance with the invention.
Figure 2:
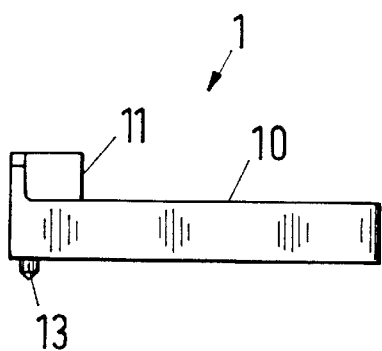
FIG. 2 is the exemplary embodiment of the tibia part in FIG. 1 in a side view.
Figure 3:
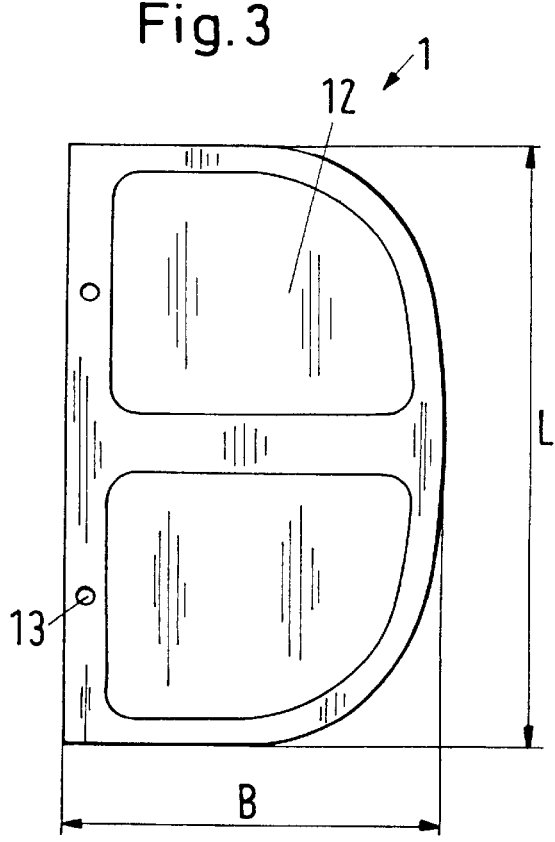
FIG. 3 is the exemplary embodiment of the tibia part in FIG. 1 in a view from below.

An exemplary embodiment of a tibia part of a mono-condylar knee joint prosthesis in accordance with the invention is illustrated in FIGS. 1–3. The tibia part 1 comprises a sliding surface 10 on which an intermediate part 2 is slidingly displaceable (see FIG. 4 and FIG. 5 respectively). A boundary wall with a boundary surface 11 which bounds the sliding surface 10 is provided at the tibia part 1. The boundary surface 11 is curved so as to be arcuate, in particular in the shape of a circular segment, and is formed in the exemplary embodiment described to be convex. The radius of curvature of this boundary surface 11 is designated by R1.

At its lower side the tibia part has cement pockets 12 (see FIG. 3) for a cemented securing of the tibia part 1 to the tibia. In principle however the tibia part can also be formed in such a manner that it has means for a cement-less anchoring in the tibia. Furthermore, one recognizes in FIG. 2 that two small fixing pins 13 project from the lower side which prevent a slipping of the tibia part 1 on the tibia in an implantation of the tibia part 1 until the bone cement has sufficiently hardened.

Figure 4:
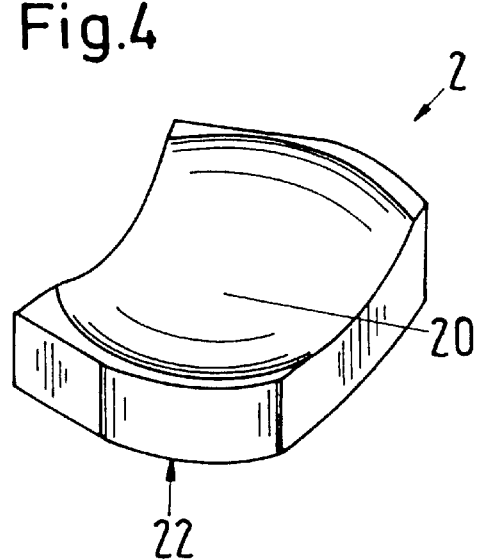
FIG. 4 is a perspective view of an intermediate part of a mono-condylar knee joint prosthesis in accordance with the invention.
Figure 5:
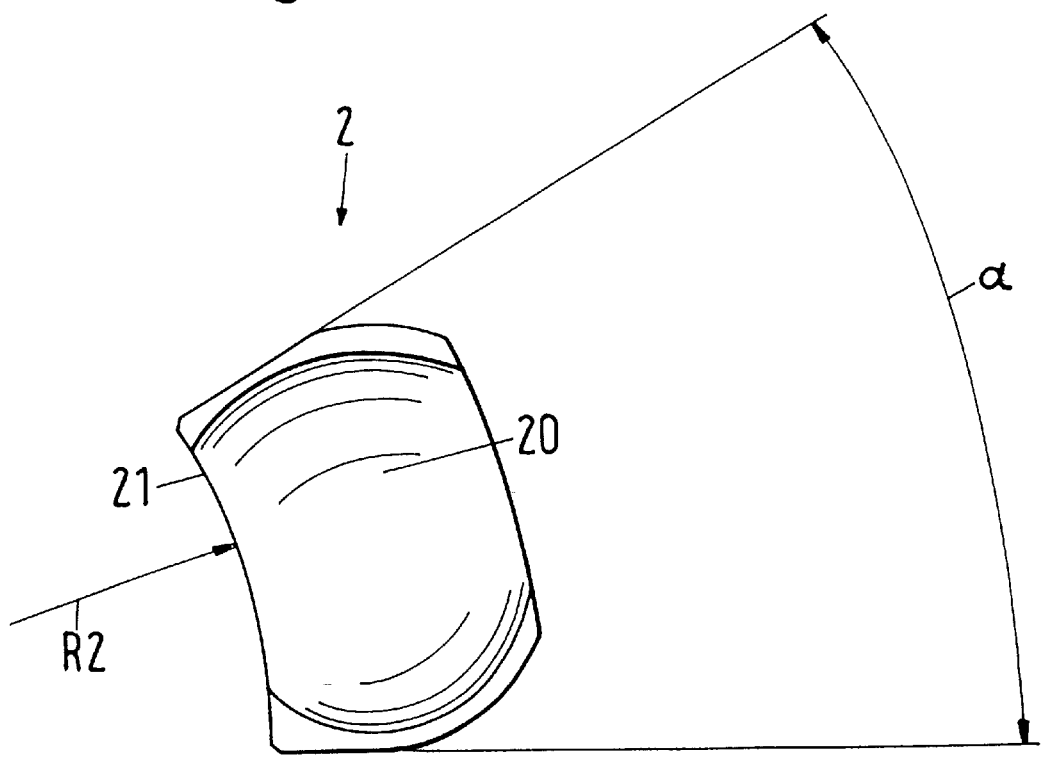
FIG. 5 is a plan view of the intermediate part of FIG. 4.

In FIG. 4 and FIG. 5 an exemplary embodiment of an intermediate part (often also designated as a "meniscus part") is illustrated, in FIG. 4 in a perspective view and in FIG. 5 in a plan view. The intermediate part 2 has a first, concave bearing surface 20 which faces the femur part 3 (see FIG. 6, FIG. 7). The concave bearing surface is preferably designed spherically and has the same radius of curvature as the running surface 30 of the femur part 3, so that maximum congruence and thus as low a surface pressing as possible result. Furthermore, the intermediate part 2 comprises a second bearing surface 22 which cooperates with the sliding surface 11 of the tibia part 1.

Furthermore, one recognizes that the intermediate part 2 has a side surface 21 which is curved so as to be arcuate, in particular to have the shape of a circular segment. The side surface 21 is formed in the described exemplary embodiment of the intermediate part 2 to be concave. The radius of curvature R2 of this concavely formed side surface 21 corresponds to the radius of curvature R1 of the convexly formed boundary surface 11 (see FIG. 1) of the tibia part 1.

Furthermore, one also recognizes that the side surface 21 extends over a specific angle of arc α. This angle of arc a preferably lies in a range from 25° to 45°. Through this on the one hand a sufficiently large side surface 21 is ensured, which can transmit forces in the medial/lateral direction to the boundary surface 11 and thereby to the tibia part 1 and thus ultimately to the tibia; and on the other hand also a sufficiently large surface for guiding the side surface 21 of the intermediate part 2 along the boundary surface 11 is ensured.

The radius of curvature R1 of the convex boundary surface 11 of the tibia part 1 and accordingly also the radius of curvature of the concave side surface 21 of the intermediate part 2 preferably lies in a range from 30–50 mm. This corresponds substantially to the conditions which occur in the natural knee or to the radii respectively by which the movement of the femoro-tibial contact point in the natural knee is particularly well approximated.

The width B of the tibia part 1 preferably lies in the range from 15–55 mm; the length L of the tibia part preferably lies in the range from 35–60 mm. Those cases of dimensions which occur in the tibia in the region of the knee in humans are thereby substantially covered.

The materials for the tibia part 1 and the intermediate part 2 are common materials which are already being used for parts of this kind. Thus the tibia part 1 is typically metallic and can e.g. be manufactured of a cobalt-chromium alloy. For the case that a cement-less implantation of the tibia part 1 is to take place the lower side of the tibia part which faces the tibia can be provided with a corresponding material layer (e.g. with a titanium layer). The intermediate part 2 is typically manufactured of a plastic such as polyethylene, in particular of ultra high molecular polyethylene, which has particularly good sliding and wear properties.

Figure 6:
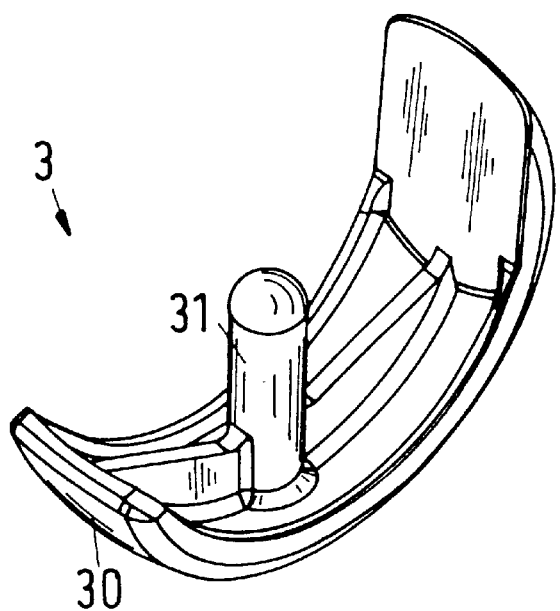
FIG. 6 is a perspective view of a femur part of a mono-condylar knee joint prosthesis in accordance with the invention.
Figure 7:
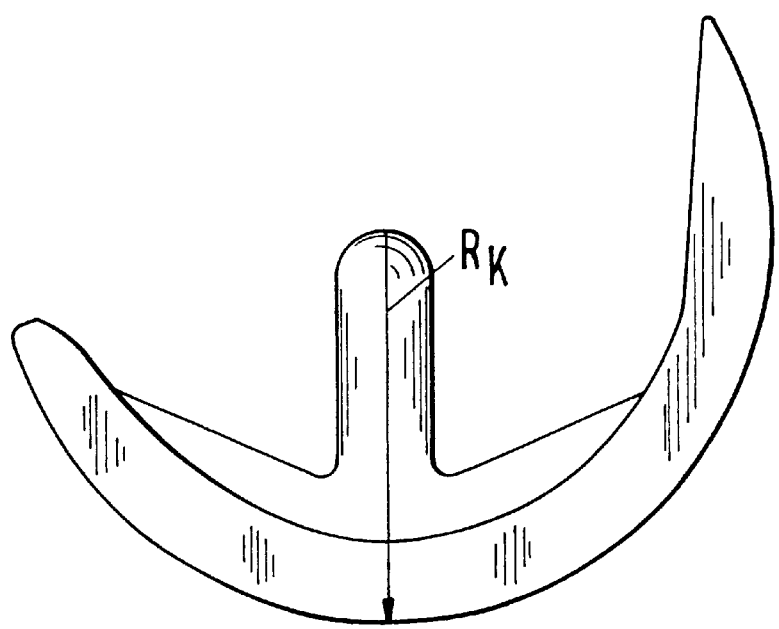
FIG. 7 is a side view of the femur part of FIG. 6.

In FIG. 6 and FIG. 7 an exemplary embodiment of a femur part 3 of the mono-condylar knee joint prosthesis in accordance with the invention is illustrated. One recognizes an anchoring pin 31 which is driven into the femur after the preparation of the femur. The running surface 30 of the femur part 3 is preferably formed spherically and has a radius of curvature $R_K$ which corresponds to the radius of curvature of the concave bearing surface 20 of the intermediate part 2 in order that maximum congruence and thus as low a surface pressing as possible result.

In regard to the material for the femur part 3 it holds that the latter is likewise manufactured of a material which is usual for such parts, e.g. of a cobalt-chromium alloy. Insofar as a cement-less implantation is to take place, those parts of the femur part 3 which come into contact with the femur (e.g. the anchoring pin 31 and the rear surface of the femur part) can be provided with a corresponding layer (e.g. a titanium layer).

What is claimed is:

1. A, mono-condylar knee joint prosthesis comprising a femur part having a convex running surface, a tibia part having a planar sliding surface which faces the femur part, and an intermediate part which is introduced between the femur part and the tibia part during implantation, said intermediate part having a first, concave bearing surface for cooperating with the convex running surface of the femur part and a second, planar bearing surface for cooperating with the sliding surface of the tibia part such that the intermediate part is slidingly displaceable on the sliding surface of the tibia part, wherein a boundary surface is provided at the tibia part on an inner side of the tibia part which bounds the sliding surface of the tibia part and projects in a direction towards the femur part in order to cooperate with a side surface of the intermediate part, wherein the boundary surface which is provided at the tibia part is curved in the shape of an arch; wherein the intermediate part has a side surface which is curved corresponding to the boundary surface which is provided at the tibia part and which is curved in the shape of an arch, wherein the boundary surface which is provided at the tibia part is curved in the shape of a convex circular segment and the side surface of the intermediate part is correspondingly curved in the shape of a concave circular segment, wherein the concave bearing surface of the intermediate part and the corresponding running surface of the femur part are each designed in the shape of a spherical segment, and wherein the side surface of the intermediate part extends over an angle of arc that lies in a range of 24 degrees to 45 degrees.

2. A knee joint prosthesis in accordance with claim 1, wherein the radius of curvature of the boundary surface of the tibia part, and accordingly the radius of curvature of the side surface of the intermediate part, lies in a range from 30–50 mm.

3. A knee joint prosthesis in accordance with claim 1, wherein the width of the tibia part lies in a range from 15–55 mm and wherein the length of the tibia part lies in a range from 35–60 mm.

* * * * *